US009545272B2

(12) United States Patent
Halanski et al.

(10) Patent No.: US 9,545,272 B2
(45) Date of Patent: Jan. 17, 2017

(54) STENT APPARATUS AND METHOD (71) Applicant: Wisconsin Alumni Research Foundation, Madison, WI (US)

(72) Inventors: Matthew Aaron Halanski, Cross Plains, WI (US); Taylor Jaraczewski, Gurnee, IL (US); Lucas Schimmelpfenning, Madison, WI (US); Stephen Kernien, Edgerton, WI (US); Cody Bindle, Plain, WI (US); Kyle Jamar, Hibbing, MN (US)

(73) Assignee: Wisconsin Alumni Research Foundation, Madison, WI (US)

( * ) Notice: Subject to any disclaimer, the term of this patent is extended or adjusted under 35 U.S.C. 154(b) by 401 days.

(21) Appl. No.: 14/010,133

(22) Filed: Aug. 26, 2013

(65) Prior Publication Data

US 2015/0057662 A1    Feb. 26, 2015

(51) Int. Cl.
*A61B 17/56* (2006.01)
*A61B 17/72* (2006.01)
*A61B 17/68* (2006.01)

(52) U.S. Cl.
CPC ....... *A61B 17/7208* (2013.01); *A61B 17/7258* (2013.01); *A61B 2017/564* (2013.01); *A61B 2017/681* (2013.01)

(58) Field of Classification Search
CPC ............ A61B 17/7266; A61B 17/7258; A61B 2017/681; A61B 17/864; A61B 17/7208; A61B 17/564

(Continued)

(56) References Cited

U.S. PATENT DOCUMENTS

2006/0085070 A1* 4/2006 Kim .................. A61B 17/7065
                                                    623/17.11
2007/0167981 A1* 7/2007 Opolski ............ A61B 17/0057
                                                    606/213

(Continued)

OTHER PUBLICATIONS

Synthes. 1998. The Titanium Elastic Nail System: Technique Guide. Adapted from <http://www.rcsed.ac.uk/fellows/lvanrensburg/classification/surgtech/ao/manuals/Synthes%20TENS%20nails.pdf> on Sep. 30, 2012.

(Continued)

*Primary Examiner* — Mary Hoffman
*Assistant Examiner* — Tara R Carter
(74) *Attorney, Agent, or Firm* — Crawford Maunu PLLC (57) ABSTRACT

A bone stent facilitates bone fixation via interior contact, as may be useful for flexible entry into a sidewall of an elongated bone. As consistent with one or more embodiments, a stent includes proximal and distal end caps connected by a plurality of elongated members extending longitudinally between the end caps, and a flexible cable extending through the proximal end cap and connected to one of the end caps. The flexible cable, end caps and elongated members are responsive to the end caps being moved toward one another by laterally bending the elongated members outwardly away from one another, with the cable fixing the elongated members in the compressed state (e.g., while applying pressure to the interior sidewalls of a bone). When the end caps are released from the compressed state, the longitudinal compressive force is released and the elongated members elastically return to the uncompressed state.

20 Claims, 8 Drawing Sheets (58) Field of Classification Search
USPC .... 606/246–249, 62–68, 300–321, 323–329; 623/17.11
See application file for complete search history.

(56) References Cited

U.S. PATENT DOCUMENTS

2008/0103528 A1* 5/2008 Zirps .................. A61B 17/0401 606/232
2009/0182336 A1* 7/2009 Brenzel .............. A61B 17/7225 606/62

OTHER PUBLICATIONS

Mashru, R. P., Herman, M. J., & Pizzutillo, P. D. (2005). Tibial shaft fractures in children and adolescents. American Academy of Orthopaedic Surgeons, 13(5), 345-352. Retrieved from http://www.jaaos.org/content/13/5/345.abstract.

Mani, U.S., et al. "Biomechanical comparison of flexible stainless steel and titanium nails with external fixation using a femur fracture model." Journal of Pediatric Orthopaedics 26.2 (2006): 182-187.

Howarth WR, Gottschalk HP, Hosalkar HS. Tibial tubercle fractures in children with intra-articular involvement: Surgical tips for Technical ease. J ChildOrthop. Dec. 2011; 5(6): 465-70.

Odéhouri-Koudou, T; Gouli, J; Yao Kreh, J; Tembély, S; Ouattara, O; et al. Elastic stable intramedullary nailing in paediatric traumatology at Yopougon Teaching Hospital. African Journal of Paediatric Surgery: AJPS 8. 2 (May 2011): 155-8.

Foster PA, Barton SB, Jones SC, Morrison RJ, Britten S. The treatment of complex tibial shaft fractures by the Ilizarov method. J Bone Joint Surg Br. Dec. 2012; 94(12): 1678-83.

He B, Wang J. Plate fixation of paediatric fractures of the distal tibia and fibula. Acta Orthop Belg. Oct. 2012; 78(5): 660-2.

Eralp L, Kocaoğlu M, Polat G, Baş A, Dirican A, Azam ME. A comparison of external fixation alone or combined with intramedullary nailing in the treatment of segmental tibial defects. Acta Orthop Belg. Oct. 2012; 78(5): 652-9.

Wheeless, Clifford, MD. 2012. Tibial Fractures: Techniques of IM Nailing. Wheeless' Textbook of Orthopaedics. <http://www.wheelessonline.com/ortho/tibial_fractures_technique_of_im_nailing>.

* cited by examiner

STENT APPARATUS AND METHOD

FIELD

Aspects of various embodiments are directed to stents and their implementation for stabilizing bones.

BACKGROUND

When a bone fracture is incurred, a number of general steps are followed to enhance healing. The bone is generally reduced in a manner that involves realigning segments of the bone into their respective anatomical locations, to ensure proper alignment and healing of the bone. The bone is then immobilized to prevent the pieces of the bone from shifting during the healing process. Immobilization may involve the use of casts or splints to hold the bones in place, generally for two to eight weeks depending on the severity and location of the break. In certain instances, traction is employed using tension to prevent the bones from shortening. In certain fractures involving long bones, traction is used to counteract large muscles that tend to pull the bone out of place. Severe cases may also require surgery with implants to keep the bones aligned during the healing process. These situations use plates and screws along with the casts to immobilize the bone.

Bone fractures and their treatment may vary greatly depending upon the bone and the patient. One type involves fracture of the tibia in children, which can be difficult to address in that the tibia is a load-bearing bone, and in that the growth plates of the tibia should be left intact. Misalignment of the tibia can lead to pain when force is placed on the bone, and can also affect the patient's gait. Similar issues can exist with other bones, such as the clavicle.

Previous techniques used for reduction and immobilization of the tibia have involved entry via an upper portion of the tibia for adults, and the use of flexible nails for pediatric patients in order to avoid growth plates. While these approaches have been useful, they can be challenging to implement in a manner that addresses the needs of the stent application. For example, when a fracture is not in the middle third of the tibia, providing a stent that appropriately supports the bone near the fracture can be difficult, particularly with pediatric patients. As another example, rotational fixation can be difficult to achieve. Furthermore, if a stent is improperly inserted or aligned, the tibial fracture can be improperly aligned, which can result in improper healing.

These and other matters have presented challenges to the treatment of bone fractures, for a variety of applications.

SUMMARY

Various example embodiments are directed to stents and their implementation.

According to an example embodiment, a stent includes proximal and distal end caps connected by a plurality of elongated members extending longitudinally between the end caps, and a flexible cable extending through the proximal end cap and connected to one of the end caps. The flexible cable, end caps and elongated members are responsive to the end caps being moved toward one another by imparting a longitudinal compressive force to the elongated members with the end caps. This longitudinal compressive force laterally bends the elongated members from an uncompressed state to a compressed state in which the end caps are closer to one another, relative to the uncompressed state, and in which the elongated members bend outwardly away from one another. The flexible cable holds the apparatus in the compressed state (e.g., by locking the end caps in place relative to one another). When the end caps are released from the compressed state, the longitudinal compressive force is released and the elongated members elastically return to the uncompressed state.

According to another example embodiment, a bone stent apparatus includes proximal and distal end caps, a plurality of elongated members extending longitudinally between the end caps, a flexible member and a flexible cable. Each elongated member has opposing ends respectively connected to one of the proximal and distal end caps. The flexible member extends in length from the proximal end cap away from the distal end cap, and has sidewalls that define an opening extending along the length. The flexible cable extends through the flexible member and the proximal end cap, the cable being connected to one of the end caps. While inserted within a bone, the cable, flexible member, end caps and elongated members operate to laterally bend the elongated members from an uncompressed state to a compressed state in response to a compressive force applied to the flexible member, via which the end caps are moved toward one another and a longitudinal compressive force is imparted to the elongated members. The elongated members bow outwardly and contact the bone in this compressed state. The apparatus returns to the uncompressed state upon release of the longitudinal compressive force, via which the elongated members elastically return to the uncompressed state in which the end caps are further away from one another, relative to a distance between the end caps in the compressed state.

Another embodiment is directed to a method in which a stent is inserted into a bone, in which the stent includes proximal and distal end caps, a plurality of elongated members extending longitudinally between the end caps, a flexible member and a flexible cable. Each elongated member has opposing ends respectively connected to one of the proximal and distal end caps. The flexible member extends in length from the proximal end cap away from the distal end cap and has sidewalls that define an opening extending along the length. The flexible cable extends through the flexible member and the proximal end cap, and is connected to one of the end caps. The elongated members are laterally bent from an uncompressed state to a compressed state by applying a compressive force to the flexible member, which moves the end caps toward one another and imparts a longitudinal compressive force to the elongated members. The elongated members bow outwardly and contact the bone in this compressed state, such as for fixating the bone. The stent is returned to the uncompressed state by releasing the longitudinal compressive force via the cable, and elastically returning the elongated members to the uncompressed state in which the end caps are further away from one another, relative to a distance between the end caps in the compressed state.

The above discussion/summary is not intended to describe each embodiment or every implementation of the present disclosure. The figures and detailed description that follow also exemplify various embodiments.

DESCRIPTION OF THE FIGURES

Various example embodiments may be more completely understood in consideration of the following detailed description in connection with the accompanying drawings, in which:

FIGS. 3A-3C show a stent apparatus in accordance with another embodiment, in which

While various embodiments discussed herein are amenable to modifications and alternative forms, aspects thereof have been shown by way of example in the drawings and will be described in detail. It should be understood, however, that the intention is not to limit the invention to the particular embodiments described. On the contrary, the intention is to cover all modifications, equivalents, and alternatives falling within the scope of the disclosure including aspects defined in the claims. In addition, the term "example" as used throughout this application is only by way of illustration, and not limitation.

DETAILED DESCRIPTION

Aspects of the present disclosure are believed to be applicable to a variety of different types of apparatuses, systems and methods involving stent applications for treating fractures. While not necessarily limited as such, various aspects may be appreciated through a discussion of examples using this context.

Various example embodiments are directed to a bone stent amenable for use in the treatment of fractures. The stent includes multiple elongated wire-like structures that extend longitudinally between respective ends. The stent expands laterally, in response to collapsing in length, in which the elongated wire-like structures bow outwardly and contact interior portions/walls of bone structure. The stent is fixed in this expanded state with the wire-like structures engaging the bone, and can be held in this position until the bone heals, after which the stent can be returned to an initial/uncompressed state and removed from the bone.

The stent is expanded and held in place in a variety of manners, to suit various applications. In some implementations, a flexible member such as a spring or flexible tube is used to apply compressive pressure to an end of the stent, with the other end being fixed. The flexible member may, for example, be inserted into the bone and apply the compressive pressure with a portion of the flexible member extending outside of the bone. In other implementations, a cable extending through one of the end regions and coupled to the other one of the end regions is used to facilitate the application of a compressive force by drawing the ends toward one another (e.g., via pulling of the cable as attached to one of the ends directly and/or via the other one of the ends).

When a flexible member is used as above, such a cable can be run through the flexible member and used to align the flexible member with an end of the stent via which the cable passes. Once the stent has been expanded, the cable can be locked in place with the flexible member (e.g., by tightening a screw), holding the stent in the expanded state. One or both ends of the stent can be further locked in place with a fastener before and/or after expansion, such as by using a pin extending into the bone. After the bone has healed, the stent can be unlocked/unfastened and removed, such as by pulling on the cable or hooking a portion of the stent with a tool and withdrawing the stent from the bone.

In more particular embodiments involving an apparatus and/or method of using such an apparatus, a bone stent apparatus includes proximal and distal end caps, elongated members extending longitudinally between and coupled to the end caps, a flexible member and a flexible cable. The flexible member contacts the proximal end cap and applies compressive force thereto, with the flexible cable passing through the flexible member, one of the end caps and extending to the other one of the end caps. The applied compressive force causes the elongated members to laterally bend/expand from an uncompressed state to a compressed state in which the end caps are closer to one another, relative to the uncompressed state. In some implementations, the cable is used to draw the distal end toward the proximal end, with the flexible member resisting/applying the compressive force that expands the stent. The stent can be held in the expanded state by locking the flexible cable to the flexible member. The apparatus returns to the uncompressed state when the longitudinal compressive force is released, with the elongated members elastically returning to an uncompressed state, with the end caps being moved away from one another as the elongated members straighten.

The above apparatus/approach can be implemented for use in a variety of bone structures, such as a tibia or clavicle. In some embodiments, a hole is made in a sidewall of a tibia and the stent is inserted into the hole while in an uncompressed state. The elongated members flex as the stent is pushed into the hole. The flexible member is extended into the hole and used to further push/align the elongated members and end caps. This approach facilitates entry of the stent into the bone from a sidewall thereof, and alignment of the stent along the length of the bone within the sidewall (e.g., about parallel to the sidewall). Once the stent is in the bone, pressure can be applied via the flexible members and/or cable to compress the end caps toward one another and thereby expand the elongated members to contact and affix the tibia. Once appropriately placed and expanded, the elongated members are locked in place. After the tibia has healed, the lock can be released, allowing the elongated members to flex/return to an uncompressed state and the stent is removed.

Figure 1A:
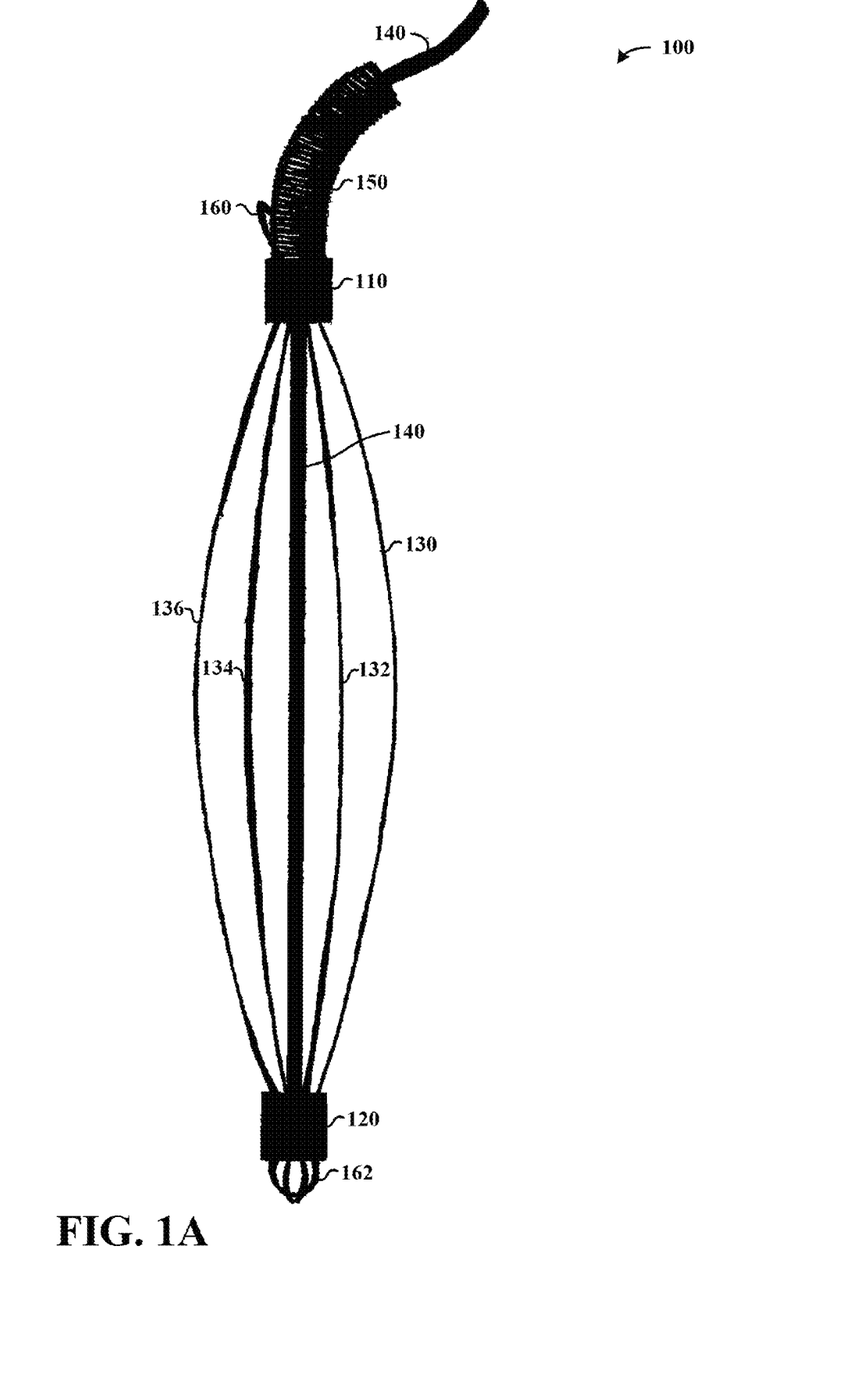
FIGS. 1A and 1B show a stent apparatus in uncompressed and compressed states, respectively, in accordance with one or more embodiments.
Figure 1B:
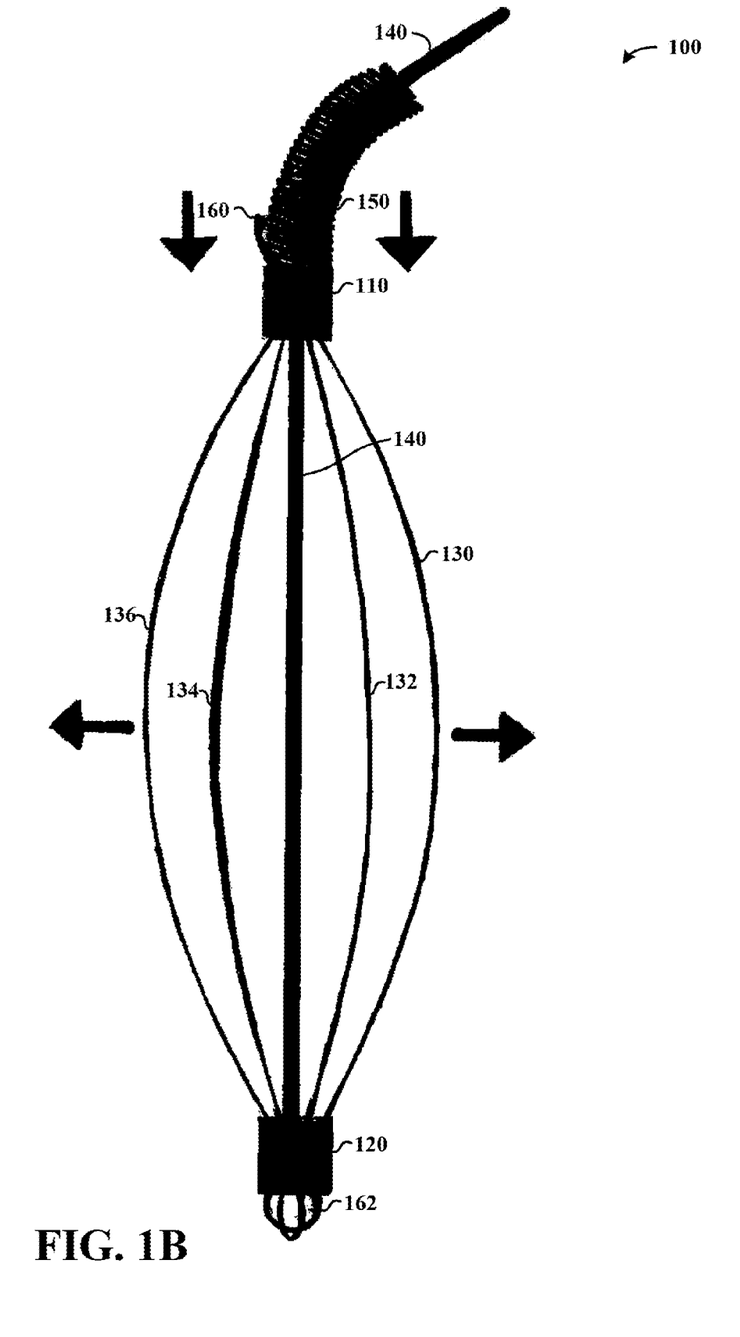

Turning now to the Figures, FIGS. 1A and 1B show a stent 100 in uncompressed and compressed states, in accordance with one or more embodiments. The stent 100 includes a proximal end cap 110, a distal end cap 120, and a plurality of elongated members 130, 132, 134 and 136 extending longitudinally between the end caps. A cable 140 passes through a flexible member 150, through the proximal end cap 110 and to the distal end cap 120. The flexible member 150 (e.g., a spring-type member, such as a spring having an outer diameter of about 0.2" and an inner diameter of about 0.12") extends in length from the proximal end cap 110 away from the distal end cap 120, and has internal sidewalls that define an opening extending along the length and via which the flexible cable passes.

FIG. 1A shows the stent 100 in an uncompressed state, in which the elongated members 130, 132, 134 and 136 are uncompressed. In this uncompressed state, the elongated members are flexible and may be passed through an opening along with the end caps (e.g., an opening slightly larger than the diameter of the end caps). The flexible member 150 laterally flexes in response to bending force applied laterally to sidewalls of the member (e.g., via bending type forces upon insertion into a bone), and is generally inflexible in response to compressive force along its length, such that it can apply a force to the proximal end cap.

In FIG. 1B, the stent 100 has been compressed, with the proximal end cap 110 being moved toward the distal end cap 120. This compression may be effected, for example, via the application of a longitudinal compressive force by the flexible member 150 to the proximal end cap 110. The elongated members bow outwardly and, when implemented within a bone, contact an interior sidewall of the bone in the compressed state (e.g., at an intermediate point of the stent). Upon release of the longitudinal compressive force, the stent 100 returns to the uncompressed state, with the elongated members being responsive to this release by elastically returning to the uncompressed state as shown in FIG. 1A and in which the end caps are further away from one another, relative to a distance between the end caps in the compressed state. In this state, the stent 100 can be removed from the bone, with the elongated members being flexible (e.g., being about parallel to one another and having an outer diameter that encompasses all of the elongated members and that is less than or about equal to a diameter of the respective end caps).

As implemented together or separately for one or more embodiments, loop-type structures 160 and 162 are shown respectively at the proximal and distal end caps 110 and 120. The loop-type structure 160 can be used, for example, for removal of the stent 100 from a bone with a hook-type tool. The loop-type structure 162 may, for example, be used to fasten the stent 100, such as by passing a pin through the bone and the loop-type structure 162.

The compressive force applied to the elongated members 130-136 is applied in a variety of manners, as may be implemented to suit particular applications. As discussed above, the compressive force may be applied via the flexible member 150, such as by advancing the flexible member against the proximal end cap 110 while the distal end cap 120 is fixed to a bone. In other implementations, the cable 140 imparts a compressive force by drawing the distal end cap 120 toward the proximal end cap 110. In still other implementations, the flexible member 150 is advanced against the proximal end cap 110, and the distal end cap 120 is drawn toward the proximal end cap via the cable 140. In yet other implementations, the cable 140 is passed through a loop at the distal end cap 120 and back to the proximal end cap 110 where the cable is fixed, with pulling on the cable effecting the drawing of the proximal end cap toward the distal end cap. After fixation, the cable 140 may be cut (e.g., near the bone) to allow the stent to remain intact in an expanded/compressed position while the bone heals.

In some implementations, the stent 100 includes an intermediate cap or other structure that limits the expansion of the elongated members 130-136, located between the proximal and distal end caps and having one or more openings therein via which the elongated members pass. In some implementations, the intermediate cap has a diameter that is about equal to or less than a diameter of one of the proximal and distal end caps and is configured and arranged to counter the bending of the flexible members when the end caps are drawn toward one another. In other implementations, the intermediate cap/structure includes a loop type structure that limits the amount of expansion of the elongated members, such as by extending with the elongated members to a diameter larger than the end caps 110 and 120.

A variety of different types of materials are used to suit various applications. In some embodiments, a stainless extension spring, stainless steel strand cable, stainless steel end cap and mid cap assembly, and stainless steel spring wire are used for the flexible member 150, cable 140, end caps 110 and 120, and loops at the end caps. Such stainless components may be grade 304 stainless, which is rated for human implantation. Other materials such as cobalt chromium and titanium may be similarly implemented.

The elongated members 130-136 are attached to the end caps 110 and 120 in a variety of manners to suit particular embodiments. In some implementations, the elongated members are welded to the end caps, such as using a TIG (tungsten inert gas) welding process. For certain applications, a small aluminum disk is placed in the middle of the stent and left in place during the welding process, then cut off after the welds have cured. This disk facilitates safe welding with small overall device diameters. For instance, a low, precise heat can be used to ensure that the stainless spring wire does not melt before adhering to the end caps. With such an approach, a 308L stainless electrode can be used in combination with Argon gas to provide a uniform sturdy weld that can be processed with an acid bath to ensure that only stainless steel remains.

Figure 2:
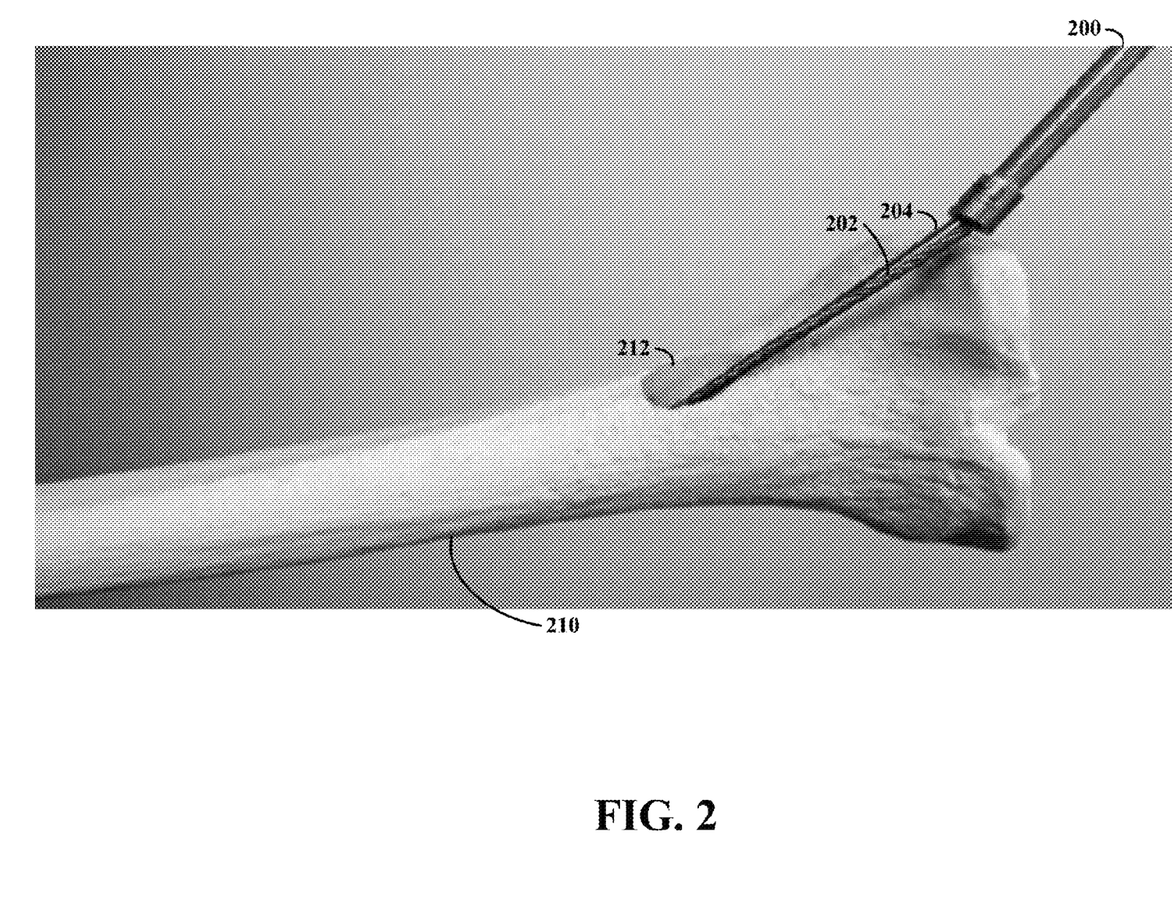
FIG. 2 shows a stent apparatus inserting into a bone in an uncompressed state, in accordance another embodiment.

FIG. 2 shows a stent 200 inserting into a bone 210 in an uncompressed state, in accordance another embodiment. The stent 200 includes a cable 202 and a plurality of elongated members extending between respective end portions, with elongated member 204 labeled by way of example, and which may be implemented in accordance with the embodiments shown in FIGS. 1A and 1B. An opening 212 is made in a sidewall of the bone, and the stent 200 is inserted therein. The elongated members and cable flex upon entry into the bone 210 via the sidewall opening 212, and align along the length of the bone within. Once in place, the elongated members can be compressed longitudinally and expanded laterally to contact interior sidewalls of the bone 210.

Figure 3A:
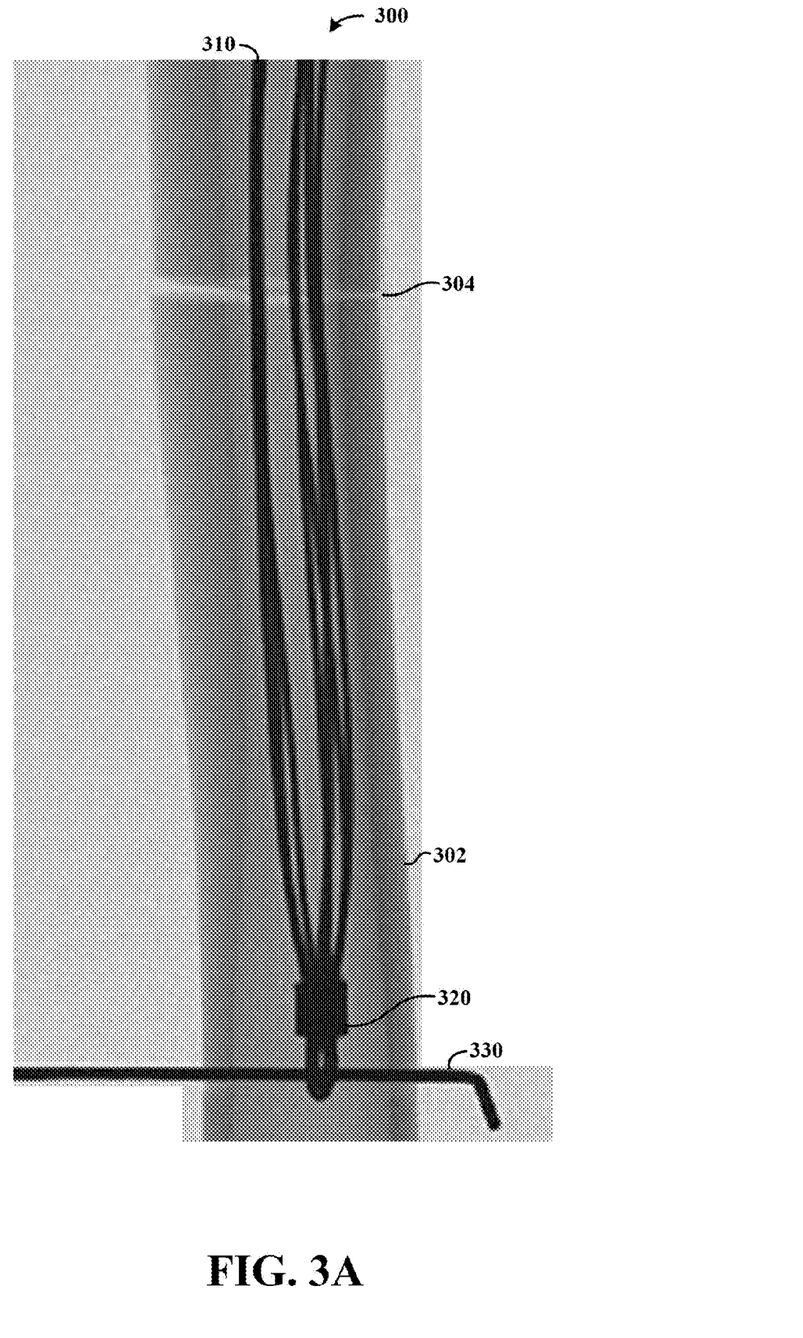
FIG. 3A shows the stent in an uncompressed state and having a distal end cap fastened to a bone with a pin.
Figure 3B:
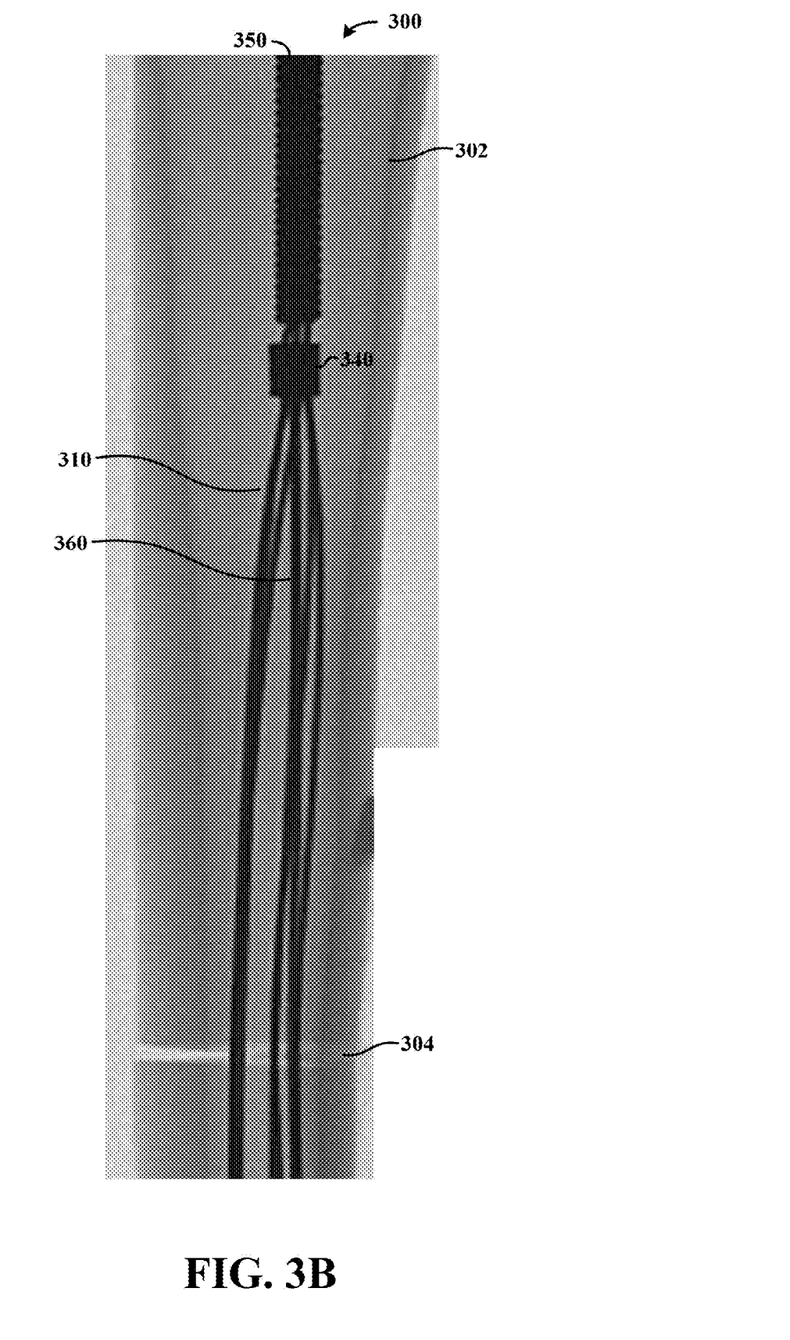
FIG. 3B shows a proximal end of the stent inserted within a bone and in an uncompressed state.
Figure 3C:
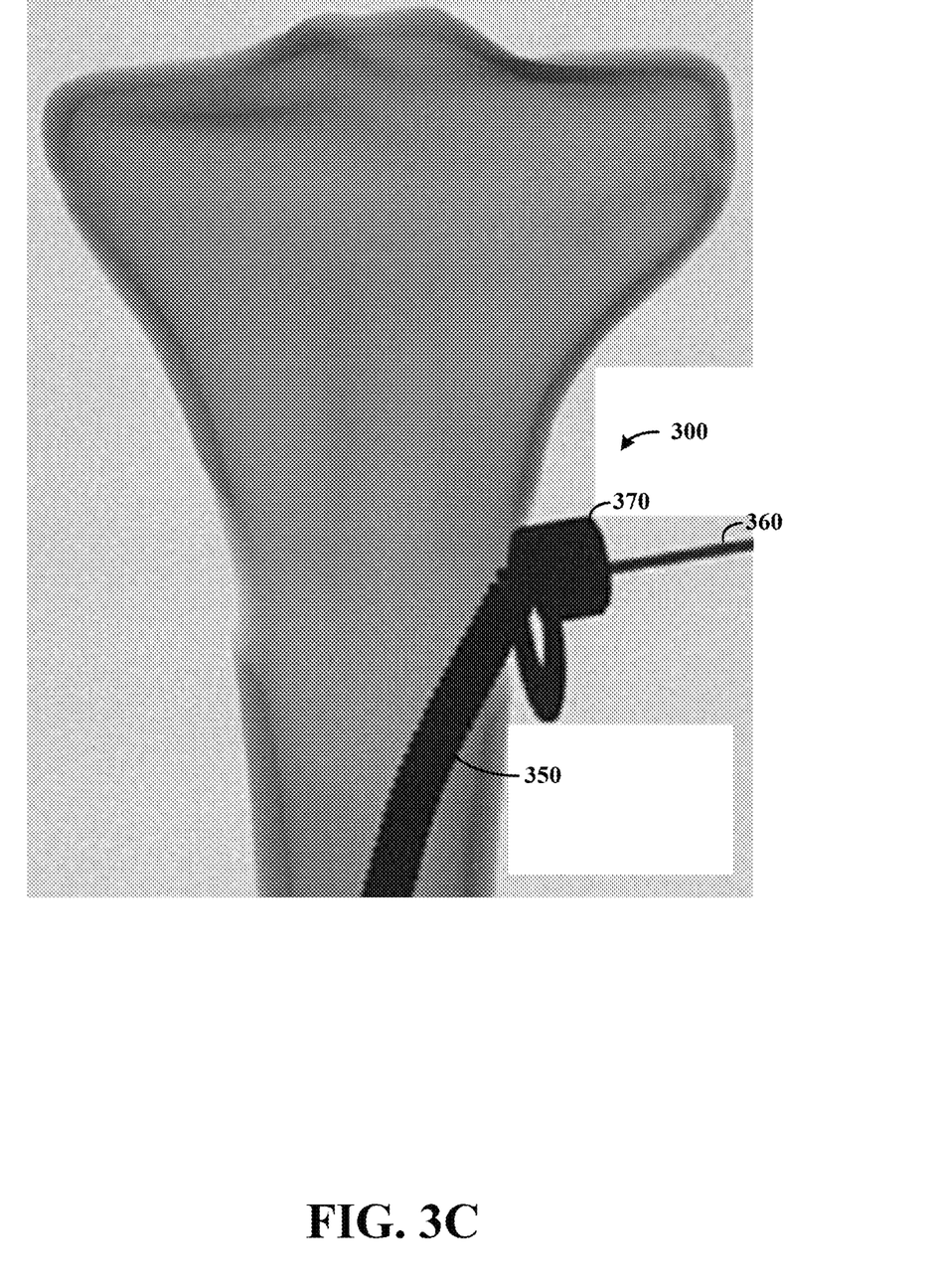
FIG. 3C shows the stent with a flexible member and cable extending out of a bone.
Figure 4:
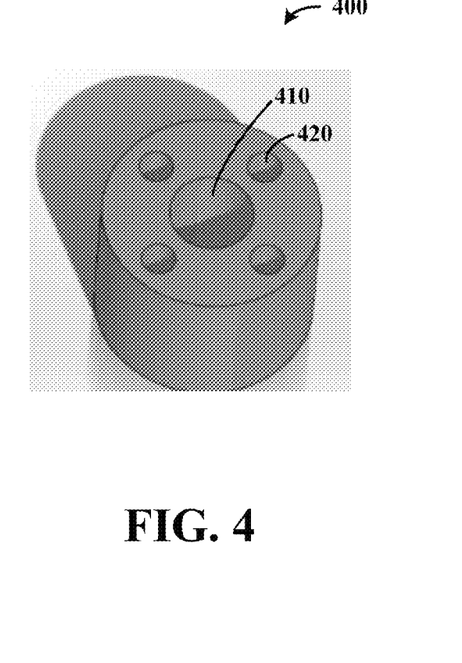
FIG. 4 shows an example four-hole end cap, in accordance with another example embodiment.

FIGS. 3A-3C show a stent 300 implemented within a bone, in accordance with other embodiments. The stent 300 may, for example, include components and/or be implemented in a manner consistent with the stent 100 shown in FIGS. 1A and 1B. Beginning with FIG. 3A, the stent 300 has been inserted within a bone 302 having a fracture at 304, and is shown in an uncompressed state. The stent 300 includes a plurality of elongated members, including elongated member 310 labeled by way of example, that extend to distal end cap 320. A pin fastener 330 holds the distal end cap 320 in place, relative to the bone 302.

Referring to FIG. 3B, a mid-portion of the stent 300 is shown within the bone 302 above the fracture 304, with the elongated members being coupled to a proximal end cap 340, and a flexible member 350 (e.g., a spring) adjacent thereto. A cable 360 extends through the proximal end cap 340 and to the distal end cap 320. The stent 300 is again shown in the uncompressed state, with the flexible member 350 arranged to apply a compressive force to the proximal end cap 340 to expand the stent.

In the uncompressed state, as applicable to FIGS. 3A and 3B, the elongated members of stent 300 may be flexibly inserted into the bone 302, such as shown in FIG. 2, and aligned in an about parallel arrangement to one another in which an outer diameter that encompasses/encircles all of the elongated members is about the same as or less than a diameter of the respective end caps 320 and 340. Pressure exerted by the flexible member 350 upon the proximal end 340 pushes the stent 300 into the bone 302.

In FIG. 3C, an upper portion of the stent 300 is shown extending into the bone 302, via a sidewall and below any growth plates. A fastener 370 secures the cable 360 upon longitudinal compression of the elongated members, and holds the stent 300 in a compressed state in which the elongated members bow outwardly, contact the bone 302 and hold the fracture 304 in place for healing. In some implementations, the fastener 370 locks to the flexible member 350. In other implementations, the fastener 370 impinges against the bone 302 under tension applied via the cable 360. The resulting expansion may, for example, be implemented in a manner similar to that shown in FIG. 1B.

A variety of end caps or other components can be implemented with stents as described herein, and such end caps/components may accommodate different quantities of elongated members and provide different fastening/coupling aspects to suit particular applications. Furthermore, the dimensions of the elongated wires can be tailored to suit various applications, such as for different bones and different patients. For instance, wires of about 0.03 inch diameter and 10 inch length can be used, with the gauge (diameter) of the wire being varied depending on the force needed in the canal. The wires can be bent at a 35 degree angle at each end (e.g., 8 mm from the tip), to ensure the wire will deform in the proper direction.

Figure 5:
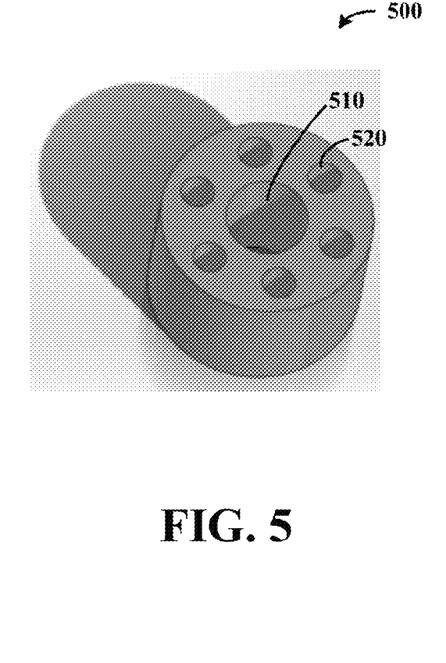
FIG. 5 shows an example six-hole end cap, in accordance with another example embodiment.
Figure 6:
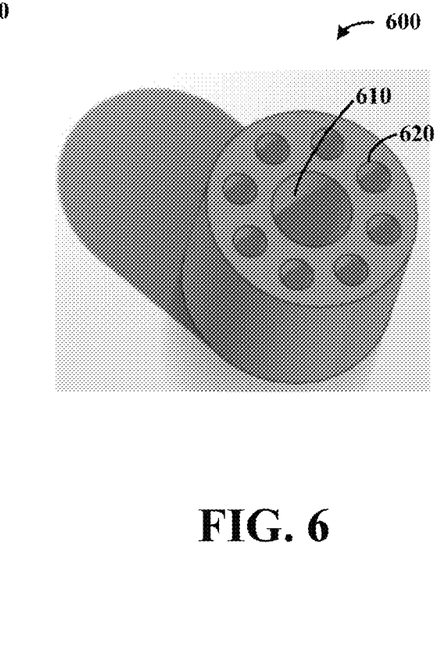
FIG. 6 shows an example eight-hole end cap, in accordance with another example embodiment.

FIGS. 4-8 show several exemplary end caps, in accordance with various embodiments. Beginning with FIG. 4, a four-hole end cap 400 is shown, in accordance with one such example embodiment. The end cap 400 includes a central opening 410 via which a cable may pass, and respective outer holes including hole 420 via which elongated members are coupled (e.g., via welding). FIG. 5 shows a six-hole end cap 500, in accordance with another example embodiment. The end cap 500 includes a central opening 510 via which a cable may pass, and respective outer holes including hole 520 via which elongated members are coupled. FIG. 6 shows an example eight-hole end cap 600, in accordance with another example embodiment. The end cap 600 includes a central opening 610 via which a cable may pass, and respective outer holes including hole 620 via which elongated members are coupled.

Figure 7:
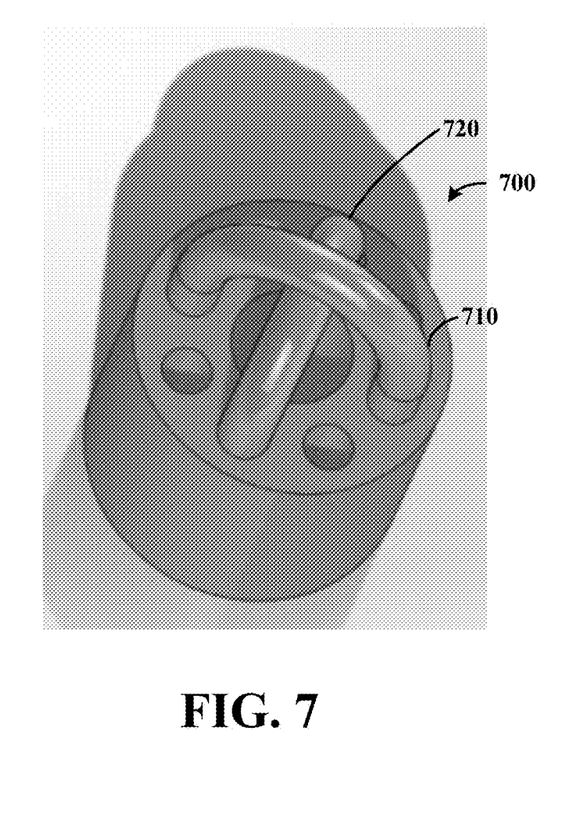
FIG. 7 shows an example end cap with looped fasteners, in accordance with another example embodiment.
Figure 8:
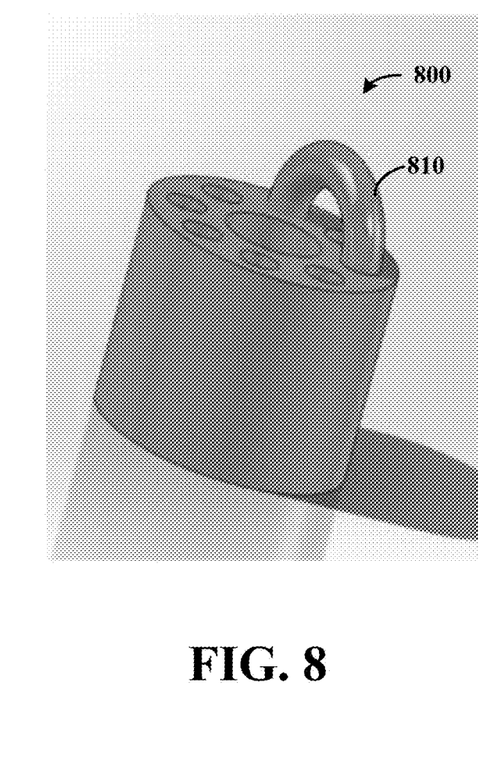
FIG. 8 shows an example end cap with a looped fastener, in accordance with another example embodiment.

FIGS. 7 and 8 show respective eight-hole end caps 700 and 800 with looped fasteners, in accordance with other example embodiments. The end cap 700 includes looped fasteners 710 and 720, and end cap 800 includes a single looped fastener 810. The end cap 700 may, for example, be used as a distal end cap that is secured via a screw or a pin such as shown in FIG. 3A, with the pin extending through one or both of the looped fasteners 710 and 720. End cap 800 may, for example, be implemented as a proximal end cap, with looped fastener 810 being implemented to facilitate withdrawal of a stent from a bone (e.g., using a hook-type tool).

Each of the end caps shown in FIGS. 4-8 may be implemented as proximal or distal end caps as discussed herein, with variations to accommodate positioning and cable passage or securement. Further, the end caps and looped fasteners shown in FIGS. 4-8 may be made in a variety of manners, using a variety of materials to suit particular applications. In some embodiments, the end caps are milled from a ¼" 304 grade stainless steel rod, which is lathed down to an outside diameter of 0.22 in. A center hole (e.g., 410) is bored on a lathe with a #50 bit. Holes (e.g., 420) are drilled around the center, evenly spaced on a mill using a 4-bolt hole pattern. A #65 bit is used, which is slightly larger than the diameter of the wire. The wires are secured in these holes with a stainless TIG weld to prevent them from spinning. The components can be machined on a lathe and mill or a CNC controller.

The amount of force to be applied to the elongated members can be tailored to suit particular applications. In some embodiments, as force is applied to expand the elongated members, an initial point type contact is made with an interior wall of a bone, after which the elongated members deform along the interior wall upon increased application of force. The normalized resultant force on the bone can be determined for both point and line contact with the following equations:

$$\text{Normalized Resultant Force: } \overline{R}\left(=\frac{R}{P}\frac{L_0}{h}\right)$$

$$\text{Point Contact: } \overline{R} = \frac{4n^2}{\left(1-\frac{2n}{\pi\varsigma}\tan\frac{\pi\varsigma}{2n}\right)}$$

$$\text{Line Contact: } \overline{R} = 2n\varsigma$$

where n is the number of buckles that occur (assumed to be 1 in this design), and ς is the normalized square root of the axial force which equals $$\varsigma \equiv \frac{kL_0}{2\pi}$$

$$k^2 \equiv \frac{P}{EI}$$

where P is the axial force, E is the elastic modulus of the material, and I is the moment of inertia of the column.

Using these equations, a theoretical resultant force R that will be exuded on bone (e.g., the intramedullary canal) with varying axial forces P, is shown as follows, with a direct relationship between the axial force and theoretical resultant force as:

$$R=-0.0004P^2+0.0874P+0.7245$$

This relationship can be implemented to set applied force for various applications, such as by manipulating different material and mechanical properties to obtain a desired resultant force.

Based upon the above discussion and illustrations, those skilled in the art will readily recognize that various modifications and changes may be made to the various embodiments without strictly following the exemplary embodiments and applications illustrated and described herein. For example, different manners of applying a force that expands the elongated members may be used, such as by pulling the cable to move the distal end cap toward the proximal end cap, or by applying a compressive force at the distal end, to suit particular embodiments. As another example, various different geometrical shapes may be implemented with the stent components such as end caps and elongated members. Such modifications do not depart from the true spirit and scope of various aspects of the invention, including aspects set forth in the claims.

What is claimed is:

1. A bone stent apparatus comprising:
a proximal end cap;
a distal end cap;
a plurality of elongated members extending longitudinally between the end caps, each elongated member having opposing ends respectively connected to one of the proximal and distal end caps;
a flexible member extending in length from the proximal end cap away from the distal end cap and having sidewalls that define an opening extending along the length; and
a flexible cable extending through the flexible member and the proximal end cap, the cable being connected to one of the end caps and configured and arranged with the flexible member, end caps and elongated members to, while inserted within a bone with the cable extending through an opening in the bone and into a proximal end of the flexible member arced toward the opening,
  laterally bend the elongated members from an uncompressed state to a compressed state by, in response to a compressive force applied to the flexible member, drawing the end caps toward one another and imparting a longitudinal compressive force to the elongated members, the elongated members bowing outwardly and contacting the bone in the compressed state, and
  return to the uncompressed state by releasing the longitudinal compressive force via the cable, the elongated members being responsive to the release of the longitudinal compressive force by elastically returning to the uncompressed state in which the end caps are further away from one another, relative to a distance between the end caps in the compressed state.

2. The apparatus of claim 1, wherein the elongated members are responsive to the compressive force by bowing outwardly at an intermediate point along the elongated members between the end caps, thereby exerting an outward force upon an interior surface of the bone.

3. The apparatus of claim 1, further including a locking fastener configured and arranged to hold the elongated members bowing outwardly and contacting the bone in the compressed state by locking the cable in place in the compressed state, the cable being configured and arranged to hold the elongated members in the compressed state.

4. The apparatus of claim 1, wherein
the cable is connected to the distal end cap,
the distal end cap is configured and arranged with a fastener that adheres to the bone and fixes the distal end cap in place, and
the flexible member is configured and arranged to apply the longitudinal compressive force to the elongated members via the proximal end cap, with the flexible member bending toward an opening in the bone via which the cable extends out of the bone.

5. The apparatus of claim 1, wherein
the cable is connected to the distal end cap, and
the flexible member and the cable are configured and arranged to apply the compressive force to the elongated members via the proximal and distal end caps.

6. The apparatus of claim 1, wherein the cable is connected to the distal end of the cap and configured and arranged to apply at least part of the compressive force in response to tension applied to the cable in the direction of the proximal cap.

7. The apparatus of claim 1, wherein the end caps have openings therein and the opposing ends of the elongated members extend into the openings and are welded to the respective end caps.

8. The apparatus of claim 1, wherein the elongated members are configured and arranged to, when in the uncompressed state, extend between the respective end caps with the elongated members being about parallel to one another and having an outer diameter that encompasses all of the elongated members and that is less than or equal to a diameter of the respective end caps.

9. The apparatus of claim 1, wherein
the elongated members are configured and arranged to, when in the uncompressed state, extend between the respective end caps with the elongated members being about parallel to one another and lying within an outer diameter that is less than or equal to a diameter of the respective end caps, and
the elongated members and end caps are configured and arranged to, when in the uncompressed state, flexibly bend upon insertion into a sidewall of the bone through a hole therein, and extend fully into the bone with the elongated members extending along a length of the bone that is about perpendicular to the sidewall, in response to pressure exerted upon the proximal end cap by the flexible member as the flexible member is pushed through the hole.

10. The apparatus of claim 1, further including an intermediate cap located between the proximal and distal end caps and having openings therein via which the elongated members pass, the intermediate cap having a diameter that is about equal or less than a diameter of one of the proximal and distal end caps and being configured and arranged to counter the bending of the flexible members when the end caps are drawn toward one another.

11. The apparatus of claim 1, wherein the flexible member is configured and arranged to laterally flex in response to bending force applied laterally to the sidewalls and inflexible in response to compressive force along its length.

12. The apparatus of claim 11, wherein the flexible member is a spring having a proximal end and a distal end that contacts the proximal end cap and imparts the compressive force thereto, the apparatus further including a locking fastener configured and arranged to hold the elongated members in the compressed state by locking the cable to the proximal end of the spring.

13. An apparatus comprising:
proximal and distal end caps connected by a plurality of elongated members extending longitudinally between the end caps;
a flexible cable extending through the proximal end cap and connected to one of the end caps; and
a flexible member having a proximal end and a distal end that contacts the proximal end cap, and having sidewalls that define an opening extending along its length,
the flexible cable, flexible member, end caps and elongated members being configured and arranged to, with the end caps and elongated members within a cylindrical structure and the flexible cable being held in or drawn through an opening in the cylindrical structure toward which the flexible member is bent,
  draw the end caps toward one another and impart a longitudinal compressive force to the elongated members with the end caps via the cable and the flexible member, using the flexible member to guide the cable along an arc and between the opening and the proximal end cap, the longitudinal compressive force laterally bending the elongated members from an uncompressed state to a compressed state in which the end caps are closer to one another than in the uncompressed state, and in which the elongated members bend outwardly away from one another and apply pressure to an internal sidewall of the cylindrical structure, the flexible cable being configured and arranged to hold the apparatus in the compressed state, and in response to the end caps being released from the compressed state, releasing the longitudinal compressive force and elastically returning the elongated members to the uncompressed state.

14. The apparatus of claim 13, wherein the flexible member is configured and arranged to move the end caps toward one another by imparting a compressive force to the proximal end cap, and further including a locking fastener configured and arranged to lock the apparatus in the compressed state by locking the cable to the proximal end of the flexible member.

15. The apparatus of claim 14, wherein the end caps and elongated members are configured and arranged to, while in the uncompressed state, extend with the elongated members between the respective end caps being about parallel to one another and having an outer diameter that encompasses all of the elongated members and that is less than or equal to a diameter of the respective end caps, and insert into a bone via an opening in a sidewall thereof, fixate respective portions of the bone in place by applying outward pressure to an interior portion of the sidewall of the bone upon the lateral bending of the elongated members to the compressed state, and elastically return to the uncompressed state and, thereafter, withdraw from the bone via the opening.

16. A method comprising:
inserting a stent into a bone, the stent having
a proximal end cap,
a distal end cap,
a plurality of elongated members extending longitudinally between the end caps, each elongated member having opposing ends respectively connected to one of the proximal and distal end caps,
a flexible member extending in length from the proximal end cap away from the distal end cap and having sidewalls that define an opening extending along the length, and
a flexible cable extending through the flexible member and the proximal end cap, the cable being connected to one of the end caps;
with the flexible member extending from an opening in the bone to the proximal end cap, laterally bending the elongated members from an uncompressed state to a compressed state by applying a compressive force to the flexible member, drawing the end caps toward one another and imparting a longitudinal compressive force to the elongated members, the elongated members bowing outwardly and contacting the bone in the compressed state; and returning the stent to the uncompressed state by releasing the longitudinal compressive force via the cable, and elastically returning the elongated members to the uncompressed state in which the end caps are further away from one another, relative to a distance between the end caps in the compressed state.

17. The method of claim 16, wherein applying the compressive force includes moving the proximal end cap toward the distal end cap by applying pressure to a portion of the flexible member external to the bone.

18. The method of claim 17, further including
locking the distal end cap in place with a fastener extending through a sidewall of the bone, and
locking the proximal end cap in place relative to the distal end cap, in the compressed state, by locking the cable at a proximal end of the flexible member at the opening in the bone.

19. A method comprising:
inserting a stent through a hole in a sidewall of a bone while the stent is in an uncompressed state, the stent including
a proximal end cap,
a distal end cap,
a plurality of elongated members extending longitudinally between the end caps, each elongated member having opposing ends respectively connected to one of the proximal and distal end caps,
a flexible member extending in length from the proximal end cap away from the distal end cap and having sidewalls that define an opening extending along the length, and
a flexible cable extending through the flexible member and the proximal end cap, the cable being connected to one of the end caps;
positioning the stent in the bone with the elongated members extending in a direction that is about parallel with the sidewall of the bone; and
laterally bending the elongated members from an uncompressed state to a compressed state by applying a compressive force to a portion of the flexible member extending outside of the bone while bending the flexible member laterally in a direction that is about perpendicular to its length, drawing the end caps toward one another and imparting a longitudinal compressive force to the elongated members, the elongated members bowing outwardly and contacting the bone in the compressed state, and locking the elongated members in place while the elongated members are in the compressed state.

20. The method of claim 19, further including
returning the stent to the uncompressed state by releasing the longitudinal compressive force via the flexible cable, and elastically returning the elongated members to the uncompressed state in which the end caps are further away from one another, relative to a distance between the end caps in the compressed state; and
removing the stent from the bone after the stent has been returned to the uncompressed state, through the hole in the sidewall of the bone.

* * * * *